United States Patent [19]

May

[11] 4,156,945
[45] Jun. 5, 1979

[54] PROSTHETIC WRIST FITTING

[75] Inventor: Denis R. W. May, London, England

[73] Assignee: J. E. Hanger & Company Limited, London, England

[21] Appl. No.: 845,748

[22] Filed: Oct. 26, 1977

[30] Foreign Application Priority Data

Nov. 18, 1976 [GB] United Kingdom ............... 48087/76

[51] Int. Cl.² ............................................. A61F 1/06
[52] U.S. Cl. ......................................... 3/12.4; 279/5; 279/76
[58] Field of Search ..................... 3/12.4, 12.5; 279/5, 279/76

[56] References Cited

U.S. PATENT DOCUMENTS

| 1,213,222 | 1/1917 | McKay | 3/12.4 |
| 1,301,367 | 4/1919 | Bowler | 3/12.4 |
| 1,319,884 | 10/1919 | McKay | 3/12.4 X |
| 1,362,793 | 12/1920 | Hirsch | 3/12.5 |
| 1,973,805 | 9/1934 | George | 3/12.4 X |
| 3,798,680 | 3/1974 | Prout | 3/12.4 |

Primary Examiner—Clifford D. Crowder
Attorney, Agent, or Firm—Pollock, VandeSande and Priddy

[57] ABSTRACT

A prosthetic wrist fitting for attachment to a fore-arm termination comprises a socket with an internally toothed ring surrounding its mouth and a complementary plug having an externally toothed ring so that the plug may be engaged with the socket in angularly adjusted relation. The plug is maintained in the socket against ejection by a spring by engagement of a keep ring slidable across the socket bore and engaging a groove in the plug. The internally toothed ring may be rotatable relatively to the body socket axis and provided with a number of over-ridable detents so that the plug may be turned through angular steps without removal from the socket. A manually operated catch retains the plug in any selected one of these adjusted steps.

6 Claims, 5 Drawing Figures

PROSTHETIC WRIST FITTING

BACKGROUND OF THE INVENTION

This invention conerns a prosthetic wrist fitting for attachment to a stump socket or to the end of an artificial arm and intended to retain a variety of terminal devices, such as an artificial hand, a double hook gripper and various tools in a manner permitting pronation and supination.

Presently available wrist fittings of the above kind are open to criticism as being undesirably heavy and difficult to operate especially by enfeebled or bilateral amputees.

The fittings of the present invention are designed to overcome these shortcomings.

SUMMARY OF THE INVENTION

According to the invention we provide a prosthetic wrist fitting comprising a body attachable to a forearm termination and including a generally cylindrical central socket with an ejector spring extending through its base, an internally toothed ring surrounding the mouth of the socket and a spring-resisted manually operable keep ring slidable transversely across the socket bore, the socket of the said body retaining a complementary plug carrying a terminal device and formed with an externally toothed ring adapted to mesh with the internally toothed ring of the socket in angularly adjusted relationship, said plug being formed with a circumferential groove engageable by the said keep ring, operation of which permits ejection of the plug.

Wrist fittings in accordance with the above definition constitute a great improvement over those currently supplied, but it will be appreciated that ejection and re-insertion of the plug is required in order to effect an angular adjustment between the body and the terminal device.

In preferred forms of fittings in accordance with the invention the necessity for removal and replacement of the plug is obviated.

Thus, in accordance with a further feature of the invention, the internally toothed ring, above referred to, is permitted to rotate relatively to the body socket axis and is provided with a number of over-ridable detents considerably fewer than the number of its teeth, so that the plug and terminal device may be turned through angular steps of significant degree.

An easily rockable catch is preferably provided to prevent undesired over-riding of the detents, so that the terminal device is firmly held in angularly adjusted position.

Regularly oriented spring pressed balls engaging slots in the periphery of the toothed ring constitute a preferred form of over-ridable detent, and the same slots may be used for engagement by the rockable catch.

The main body of the wrist fitting is preferably made from aluminum alloy, while subsidiary elements are made from steel or plastics material depending upon the strength requirements of their duties.

It is a feature of the fitting that a standard socket and plug can be used for a range of sizes suitable for children, women and men.

DESCRIPTION

Figure 1:
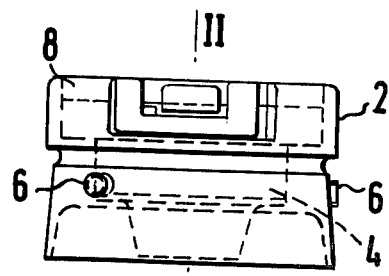
FIG. 1 is a side elevation of a complete fitting.

In FIG. 1 an outer, generally cylindrical casing 2 for fixing by lamination to a forearm termination is shown fitted around a sub-assembly 4, indicated by broken lines. Both the casing and the main body of the sub-assembly are made from aluminum and are secured together by grub screws 6. An annular plastics cover plate 8 is secured to the main body of the sub-assembly by counter-sunk screws (not shown).

Figure 2:
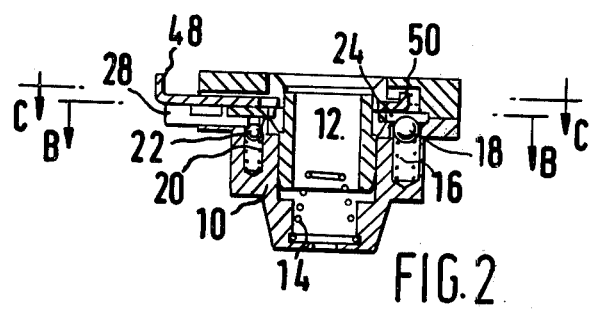
FIG. 2 is a central vertical section of a subassembly of the fitting of FIG. 1 on the line II—II and with the cylindrical casing removed.

Next considering FIG. 2, the aluminum main body 10 of the sub-assembly is formed with a generally cylindrical central socket 12, which is slightly outwardly belled towards its upper end.

A conical compression spring 14 is fitted in the base of the socket 12 for plug ejectment as will be described hereafter.

A series of three regularly spaced vertical holes in the body 10 receive springs 16 and steel balls 18, while a smaller hole receives a spring 20 and ball 22.

Figure 4:
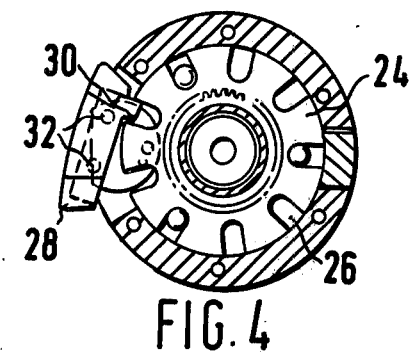
FIG. 4 is a horizontal section on the line B—B of FIG. 2.

Immediately above the top surface of the socket 12 is fitted an internally toothed ring 24, best seen in FIG. 4. This ring has, say, thirty six teeth, which protrude into the upper belled portion of the socket.

The outer circumference of the ring 24 is formed with nine slots 26 (FIG. 4), into which the balls 18 intrude to give an over-ridable detent against rotation about the socket axis.

A rockable catch 28, formed with a claw 30 and two undersurface indents 32, is pivoted to the body 10 above the ball 22 in such manner that its claw 30 may be engaged or disengaged with one or another of the slots 26 in the ring 24 with a "click" action. Thus the ring 24 may be rotated relative to the axis of the socket 12 in 40 degrees steps over the balls 18 and may be locked in a chosen position.

Figure 5:
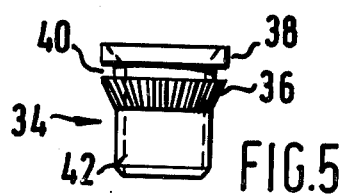
FIG. 5 is a side elevation of a plug for use with the fitting.

A plug 34 for insertion into the socket 12 is shown in FIG. 5. It is formed with an externally toothed frustoconical ring 36 adapted to engage the teeth of the ring 24 at any of 10 degrees angular dispositions.

Between the toothed ring 36 and a shoulder 38 is a groove 40.

The plug 34 is centrally drilled and threaded at 42 and the upper end of the central bore is countersunk.

The thread of the plug 34 is adapted to receive the standard threaded end of a range of currently available terminal devices. A variety of devices are each provided with a plug 34 as above described for insertion into the first fitting.

Figure 3:
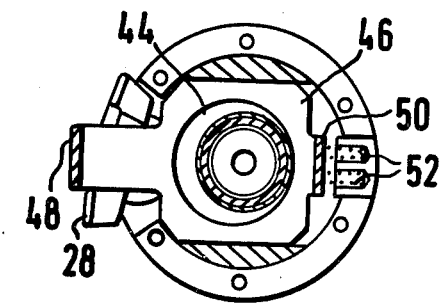
FIG. 3 is a horizontal section on the line C—C of FIG. 2.

Next considering FIG. 3, a keep ring 44 of greater diameter than the open mouth of the socket 12 is formed in a slide plate 46 fitted with a finger-press extension 48. The opposite end 50 of the plate is upwardly bent and bears against a pair of small compression springs 52, so that it is normally pushed out into the position shown in FIG. 3.

When the plug 34 of a terminal device is entered into the mouth of the socket 12 and is pressed inwardly against the pressure of the spring 14, the keep ring 44 in the plate 46 is displaced against the springs 52 by the frusto-conical ring 36 of the plug as its teeth engage the teeth of the toothed ring 24. When the two sets of teeth are fully in mesh, the groove 40 comes opposite the keep ring 44 and is firmly engaged thereby as it is returned to its normal position by the springs 52.

The terminal device is thus locked firmly into the wrist fitting.

Release of the claw 30 of the rockable catch 28 from a slot 26 enables the terminal device to be rotated with the ring 24 in defined steps relative to the wrist fitting.

Operation of the finger-press extension 48 of the plate 46 disengages the keep ring 44 from the groove 40 of the terminal device plug 34 and this is ejected by the spring 14.

It will be understood that the invention is not restricted to the details of the preferred form described by way of example which may be modified without departure from the scope of the accompanying claims.

I claim:

1. A prosthetic wrist fitting comprising a casing attachable to a forearm termination, and a sub-unit insertable into said casing and fixable in relation thereto, said sub-unit comprising a main body, a generally cylindrical central socket in said body, an ejector spring disposed adjacent the base of said socket, an internally toothed ring surrounding the mouth of said socket, a plug complementary to said socket and carrying a terminal device, an externally toothed ring on said plug meshable with said internally toothed ring, a circumferential groove around said plug, a spring resisted keep ring slidable transversely across the bore of said socket and engageable with said groove in said plug, and manually operable means to disengage said keep ring from said groove to permit ejection of said plug from said socket by said ejector spring.

2. A prosthetic wrist fitting as defined in claim 1, wherein said internally toothed ring is rotatable about the socket axis to any one of a plurality of angular positions, and over-ridable detents for locating and maintaining the internally toothed ring in selected angular positions.

3. A prosthetic wrist fitting as defined in claim 2, wherein said over-ridable detents comprise a plurality of regularly spaced spring pressed balls engaging slots in the periphery of said internally toothed ring.

4. A prosthetic wrist fitting as defined in claim 3, including a catch engaging one of said slots to prevent overriding of said detents and to maintain the terminal device in a desired angularly adjusted position, and further manually operable means to disengage the catch from said one of said slots to permit rotation of the terminal device.

5. A prosthetic wrist fitting as defined in claim 1, wherein said keep ring is formed in a slide plate, said manually operable means comprising a finger-press member extending from one side of said slide plate, an upturned portion in said slide plate at the opposite side thereof, and spring means bearing on said upturned portion of said slide plate to bias said plate slidably to a position in which said keep ring engages said circumferential groove in said plug.

6. A prosthetic wrist fitting comprising a body attachable to a forearm termination, a generally cylindrical central socket in said body, an ejector spring disposed adjacent the base of said socket, an internally toothed ring surrounding the mouth of said socket, said internally toothed ring being rotatable about the axis of said socket to any one of a plurality of angular positions, overridable detents for locating and maintaining said internally toothed ring in selected angular positions, a catch for preventing overriding of said detents, manually operable means to disengage said catch, said catch including indents cooperating with a spring-pressed member engageable in said indents whereby a click is produced on operation of said catch, a plug complementary to said socket, said plug carrying a terminal device, an externally toothed ring on said plug meshable with said internally toothed ring, a circumferential groove around said plug, a spring resisted keep ring slidable transversely across the bore of said socket and engageable with said groove in said plug, and manually operable means for disengaging said keep ring from said groove to permit ejection of said plug from said socket by said ejector spring.

* * * * *